(12) United States Patent
Gevins et al.

(10) Patent No.: US 6,445,940 B1
(45) Date of Patent: Sep. 3, 2002

(54) CERAMIC SINGLE-PLATE CAPACITOR EEG ELECTRODE

(75) Inventors: Alan S. Gevins, San Francisco; David Blau, Saratoga, both of CA (US)

(73) Assignee: Sam Technology, Inc., San Francisco, CA (US)

( * ) Notice: Subject to any disclaimer, the term of this patent is extended or adjusted under 35 U.S.C. 154(b) by 139 days.

(21) Appl. No.: 09/637,077

(22) Filed: Aug. 11, 2000

(51) Int. Cl.⁷ .................................................. A61B 5/04
(52) U.S. Cl. ........................ 600/382; 600/544; 600/383
(58) Field of Search ................. 600/544, 545, 600/546, 372, 382, 383

(56) References Cited

U.S. PATENT DOCUMENTS

| | | | |
|---|---|---|---|
| 4,683,892 A | 8/1987 | Johansson et al. | |
| 4,709,702 A | 12/1987 | Sherwin | 128/644 |
| 5,038,782 A | 8/1991 | Gevins et al. | 128/644 |
| 5,479,934 A | * 1/1996 | Imran | 128/731 |
| 6,067,464 A | * 5/2000 | Musha | 600/383 |
| 6,155,974 A | * 12/2000 | Fish | 600/544 |
| 6,171,239 B1 | * 1/2001 | Humphrey | 600/372 |

FOREIGN PATENT DOCUMENTS

CA 2280996 * 8/1999

OTHER PUBLICATIONS

Taheri et al, "A dry electrode for EEG recording" Elect. & Cl. Neurophysiology 90 (1994) 376–383.
Prutchi et al, "New Technologies for In–Flight Pasteless Bioelectrodes" Aviation Space Environ.Med. 64 (1993) 552–556.

* cited by examiner

*Primary Examiner*—Linda C. M. Dvorak
*Assistant Examiner*—David M Reddy
(74) *Attorney, Agent, or Firm*—Eliot S. Gerber, Esq; Fay Kaplun & Marcin LLP

(57) ABSTRACT

A dry electrode, which is a single-plate capacitor, is particularly adapted to be placed on a patient's scalp to detect brain waves in an EEG system. The electrode comprises a metal disk sandwiched between very thin and relatively thicker layers of ceramic. The metal disk is attached to a small disk printed circuit board that carries an amplifier to amplify the brain waves detected by the electrode. The quality of contact of the electrode with the patient is measured by applying a pulse or voltage step through the ground electrode.

15 Claims, 5 Drawing Sheets

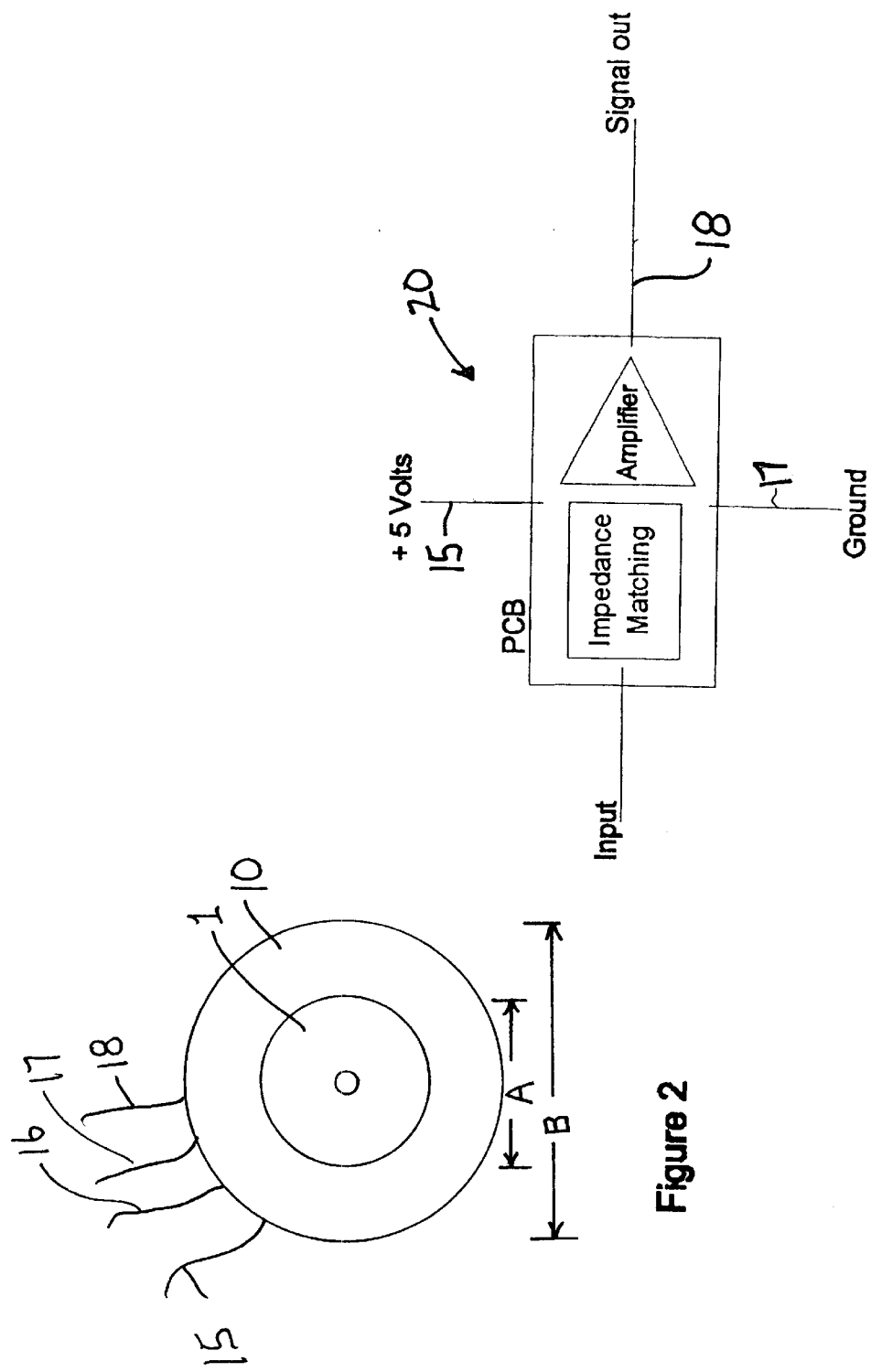

CERAMIC SINGLE-PLATE CAPACITOR EEG ELECTRODE

This invention was made with Government support under Contract F41624-97-C-6030 awarded by the Air Force Research Laboratory. The government has certain rights in the invention.

BACKGROUND OF THE INVENTION

1. Field of the Invention

The present invention relates to non-invasive skin contact electrodes for measuring bioelectrical signals from the human body, particularly to electrodes applied to the scalp for the measurement of electroencephalogram (EEG) signals from the human brain.

2. Description of the Related Art

Conventional techniques for recording brain waves (electroencephalograms for EEGs) of a human subject require connecting electrodes on the scalp with a low impedance connection. This generally involves cleaning and abrading the scalp and applying a conducting gel or solution that makes the electrical contact between the scalp and the electrode. When performed manually, the procedure takes about 20 minutes for the nineteen electrodes usually used in clinical EEG examinations, and correspondingly longer when more electrodes are used for high resolution recordings.

Prior attempts to make the process of attaching electrodes to the scalp more efficient have met with limited success. A device by Johannson, Eralp and Ital (U.S. Pat. No. 4,683,892) is based on an electromechanical design which mechanized the manual scalp preparation procedure. Due to its bulk, weight and mechanical complexity, the device had limited utility.

In U.S. Pat. No. 4,709,702 to Sherwin, the electrodes contact the scalp with "tulip probes" having sharp points to "penetrate the dead skin layer." Such a sharp point tip is medically dangerous due to the possibility of infection and hurting the patient.

In U.S. Pat. No. 5,038,782 to Gevins, Durousseau and Libove, a dry electrode is described in which multiple metal conductive fingers protrude through the hair to the scalp. Because of the high impedance connection of the electrode tips with the scalp, the electrodes are excessively sensitive to artifacts resulting from head motion.

Taheri, Knight and Smith, "A dry electrode for EEG recording", *Elect. & Cl. Neurophysiology* 90 (1994), 376–383, describe a dry electrode in which one side of a 3 mm stainless steel disk is covered with a 200 nanometer thick silicon nitride coating that contacts the skin. The thin coating is fragile and easily damaged by handling, or by repeated or prolonged contact with the scalp. It is also difficult and therefore expensive to manufacture such a coating with the very low level of contaminants required for a capacitive electrode. The device attempts to compensate for poor quality electrode contact by using complex electronic circuits to sample multiple contacts to find the best one at any given instant.

Prutchi and Sagi-Dolev, "New Technologies for In-Flight Pasteless Bioelectrodes," *Aviat. Space Environ. Med.* 64 (1993) 552–556, describe a dry electrode using an aluminum plate with a hard aluminum oxide coating applied by a novel anodization process. The coating is subject to contamination by salt from the skin and also to scratching because it is very thin, rendering the device not practical.

SUMMARY OF THE INVENTION

In accordance with the present invention, a novel device called "Ceramic Single Plate Capacitor EEG Electrode" is provided for measuring electrical potentials from the scalp or surface of the body.

The Ceramic Single Plate Capacitor EEG Electrode is a capacitive electrode. It is implemented as a capacitor with a single internal conducting plate, rather than the usual two plates of a conventional capacitor. The conducting plate is covered by a very high dielectric constant ceramic layer that acts as the insulating medium. Typically the relative dielectric constant is as great as 20,000. The conducting plate is separated from the patient's scalp by the insulating ceramic layer. When placed in close proximity to the scalp, the patient's brain in effect acts as the second plate of the capacitor. The "ceramic" is normally a transition metal oxide composition which is generally formed by firing at a high temperature, i.e., sintered.

The main advantage of this electrode is that it measures brain waves or other physiological potentials without the need to cleanse and abrade the skin or apply conducting gels or liquids. The electrode can consequently be applied very quickly, and problems associated with the mess of the electrode gel and drying out of the electrode gel in long duration recordings are eliminated. Another advantage of the present electrode is that the possibility of shocking the patient through the electrode is virtually eliminated due to the high electrical isolation of the insulating ceramic layer. Additionally, electrolytic voltages generated in conventional wet electrodes by the virtual battery formed between the skin, the electrode gel, and the electrode, are eliminated. This, in principle, reduces artifacts due to head and body movements. The ceramic layer is relatively thick, 0.1 to 1.0 mm, hard and abrasion resistant. It has high capacitance (approximately 10–30 nanofarads). The ceramic layer, unlike thin film capacitors such as those that use silicon nitride, can withstand the mechanical abrasion that occurs in routine use without shorting out the capacitor. Because a robust contact is made, only a single contact point is necessary. Therefore, complex electronic circuits that sample multiple contacts in order to find a good one are unnecessary. Additionally, the electrode of the present invention may be manufactured inexpensively since the electrode is the equivalent of a parallel plate capacitor with one plate missing. It can be manufactured using conventional ceramic capacitor manufacturing facilities.

The ceramic electrode is preferably mounted on a miniature conventional printed circuit board with a preamplifier (using standard methods) and the entire assembly can be encapsulated and positioned on the head, or body, of the patient. The preamp buffers the high impedance signal from the electrode, drives the cable, and supplies some shielding of the electrode with its internal ground plane. Additional shielding is provided by a cap or electrode holder that keeps the electrode in contact with the patient.

The contact quality and electrical gain characteristics of the electrode-to-patient contact can be ascertained using a small injected signal on the patient ground contact. This provides a means of automatically checking the electrode hookup for problems. The idea is to apply a unit step of a few millivolts on the ground electrode of the patient. The RC network formed by the input resistor on the preamplifier and the capacitor electrode causes a decay in the voltage out of the preamplifier. If the contact to the patient is good, this capacity is high, in the 10 nanofarad range, and the circuit time constant is long. If the contact is poor, this capacity drops and is measured as a short time constant. This decay provides the information needed to compensate the electrode gain at low frequencies, and indicates if the capacity is less than expected because of poor contact quality. There is also a quick discharge phase that can be measured to determine the contact quality as well. The quick discharge phase can indicate the electrode has an area that is not in contact with the patient.

OBJECTIVES AND FEATURES OF THE INVENTION

It is the objective of the present invention to provide an electrode to:
1. Record brain waves, or other physiological electrical potentials from the body, without the need to cleanse and abrade the skin or applying conducting gels or liquids;
2. Provide an electrode with high resistivity and capacitance;
3. Provide an electrode with a surface that is resistant to mechanical abrasion, to permit long duration recordings or repeated recordings;
4. Provide an electrode that is relatively simple and inexpensive to manufacture;
5. Provide an electrode that can be mounted on a conventional miniature printed circuit board, along with a preamplifier, using standard manufacturing methods;
6. Provide an electrode and amplifier assembly that can be encapsulated and positioned on a patient's head, or body, in order to minimize interference from ambient electrical noise and to generate a low impedance output signal that is relatively insensitive to interference; and
7. Provide a means of automatically measuring the quality (impedance) of the contact between the electrode and the patient using a small injected signal on the patient ground contact.

It is a feature of the present invention to record brain waves, or other physiological electrical potentials, without the need to cleanse and abrade the skin conducting gels or liquids.

It is a further feature of the present invention to provide an electrode with a very high resistivity (greater than 100 Giga-ohm) and capacitance (approximately 30 nanofarads).

It is a further feature of the present invention to provide an electrode with a ceramic surface that is resistant to mechanical abrasion so that it may be used for long duration recordings, used multiple times, and cleaned and reused easily with conventional methods.

It is a further feature of the present invention to provide an electrode that is relatively simple and inexpensive to manufacture.

It is a further feature of the present invention to provide an electrode that can be mounted on a conventional miniature printed circuit board, along with a preamplifier, using standard manufacturing methods.

It is a further feature of the present invention to provide an electrode and amplifier assembly that can be encapsulated and positioned on a patient in order to provide immunity to ambient electrical noise and to generate a low impedance output signal that is relatively insensitive to interference.

It is a further feature of the present invention to provide a means of measuring the quality of the contact between the electrode and the patient using a small injected signal on the patient ground contact.

It is a further feature of the present invention to provide an electrode in which special electrode shapes are possible. For example, the ceramic can be shaped to have bumps or grooves to part the hair, be long and narrow or triangular to separate the hair during application, etc.

BRIEF DESCRIPTION OF THE DRAWINGS

Other objectives and features of the present invention will be apparent from the following detailed description, taken in conjunction with the accompanying drawings.

In the drawings:

FIG. 2 is a bottom plan view of the assembly of FIG. 1;

FIG. 5 is a block diagram for the preamplifier;

DETAILED DESCRIPTION OF THE INVENTION

Figure 3:
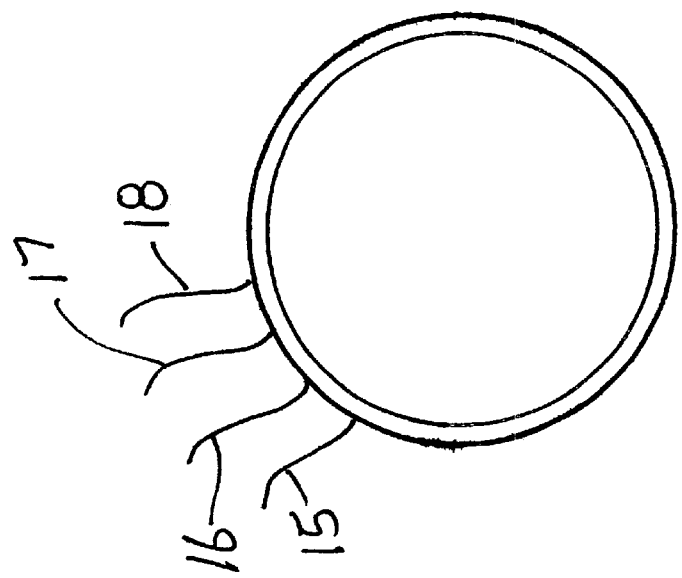
FIG. 3 is a top plan view of the assembly of FIG. 1.
Figure 1:
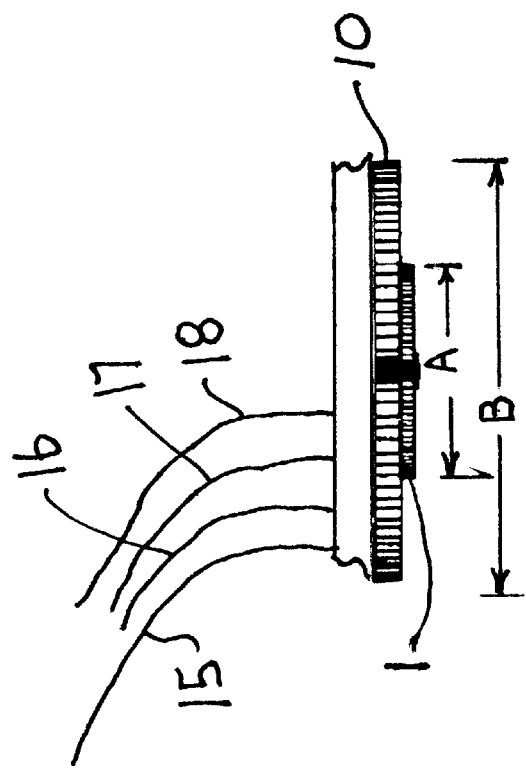
FIG. 1 is a side plan view of the assembly comprising the single-plate capacitor electrode of the present invention mounted in the printed circuit board with a preamplifier.
Figure 1B:
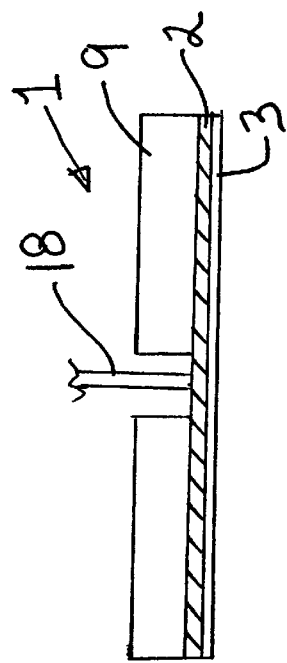
FIG. 1B is a side plan view (enlarged) of the single-plate capacitor electrode showing the metalization layer for the electrode sandwiched between two ceramic layers, a thinner ceramic electrode capacitor layer that contacts the patient's skin and a thicker ceramic backing layer that provides mechanical strength.

The present invention is illustrated in FIGS. 1–5A. As shown therein, the electrode 1 consists of a metalized dielectric disk, preferably in the range of 2–10 mm in diameter, more preferably in the range of 3.5–5 mm in diameter and most preferably about 4.3 mm in diameter ("A" in FIG. 2). The electrode is implemented as a ceramic capacitor with a single internal conductive plate 2. A ceramic capacitor insulator 3 is the bottom layer. It is very thin, normally 0.1 to 0.5 mm. This dielectric layer achieves a resistivity of greater than 100 giga-ohms and a capacitance of approximately 10–30 nanofarads, i.e., 20 nanofarads.

Since the ceramic capacitor insulator is as thin as 0.002 inches and potentially subject to breakage due to the ceramic's brittle nature, the ceramic is manufactured as a sandwich, like a hamburger, with the electrode in the middle and a second layer 9 of ceramic, as thick as 3 mm, as a backing (see FIG. 1A). The backing ceramic has a hole through which contact to the electrode plate is made. The contact can either be soldered to the printed circuit board with a wire, or attached with a spring contact when removal of the electrode is desired. The electrode is soldered to a preamplification printed circuit board that, in one example, is 8.9 mm in diameter and is preferably in the range of 5–13 mm in diameter. In an alternative embodiment, the electrode plugs into a socket in the preamplification printed circuit board in order to allow the electrode to be removed and replaced by the user, for example, for hygienic purposes. Epoxy covers the printed circuit board to seal it from moisture.

The insulative ceramic dielectric 3 of the capacitor is preferably approximately 0.03 inches (0.76 mm) thick and in the range of 0.1 to 1 mm thick, and is preferably made of "Y5V" material. That material is available from TAM Ceramics, Inc., Niagara Falls, N.Y., and is described as Y5V183. The ceramic dielectric actually is formed in two layers, and the metal layer, made of palladium/silver, is placed between the two layers. The top layer of ceramic is relatively thick, and the bottom layer is very thin, nominally 0.002" to 0.005". The dielectric achieves a resistivity of greater than 100 giga-ohms and a capacitance of approximately 20 nanofarads.

The preamplifier 10 buffers the signals generated by the capacitive electrode 1; i.e., it converts the high impedance electrode signal (i.e., one giga-ohm) into a low impedance output signal (e.g. 100 ohms) suitable for input to conventional EEG amplifiers. The printed circuit board 13 provides a ground plane that shields the capacitive electrode 1 from environmental electrical noise. An additional conductive shield 11 of typically 1"×1" directly over the printed circuit board provides further shielding. The capacitive electrode 1 is preferably used in a differential configuration to minimize electrical noise picked up by the body. A conventional wet ground electrode is preferably used to complete the capacitor circuit. Alternatively, a pair of dry capacitive electrodes, of the present invention, placed approximately 2 cm apart, can be used as a ground.

As shown in FIG. 5, the preamplifier 20 is a very low noise FET (Field Effect Transistor) input follower (gain of 1), which buffers the high impedance (approximately one giga-ohm) from the electrode into a low impedance output signal 18 (i.e.100 ohms) to the EEG amplifiers. This makes the output signal of the device immune to electrical interference. The bottom 12 of the board 13 is un-plated except for the electrode contact pad and the electrode 1 is attached to it with epoxy. The board 13, in this embodiment, has a diameter of 8.9 mm ("B" in FIG. 2). The wire lead 14 from the electrode passes through a central hole in the board 13 and makes contact with the input connector for the preamplifier. There are no holes or plating on the bottom of the board, to avoid shorting the circuit by contact with the patient, or else any through holes are insulated with epoxy when the electrode is attached. The wires, which supply voltage (+5 volts on wire 15 and −5 volts on wire 16), the ground connection 17 and the output signal 18 are blind and the wires break off from the top of the board 13. The board 13 also has grounded pads around the edge that can be used to solder the board into a cap.

Figure 5A:
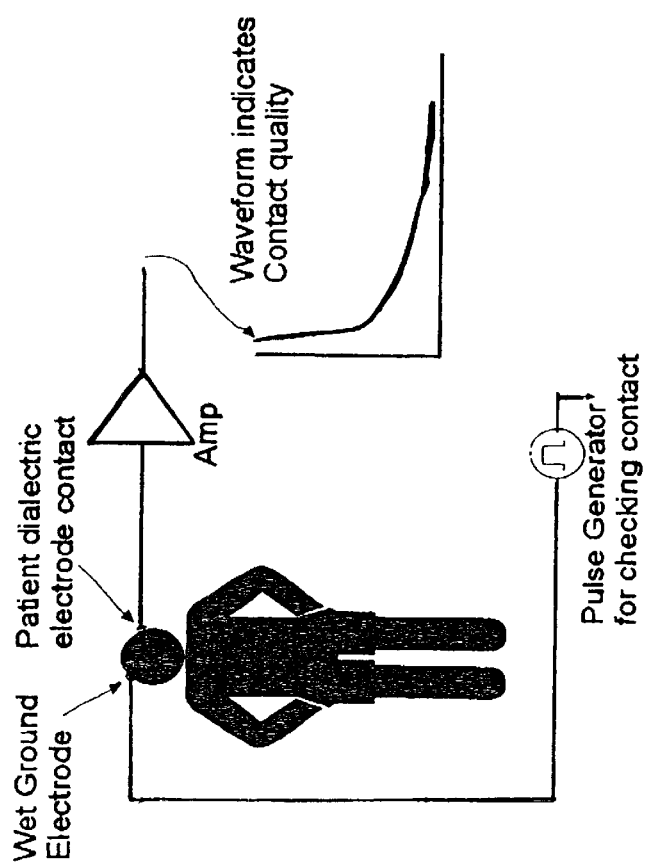
FIG. 5A is a schematic diagram showing the method of checking electrode contact quality by injecting a pulse on the ground electrode.
Figure 4:
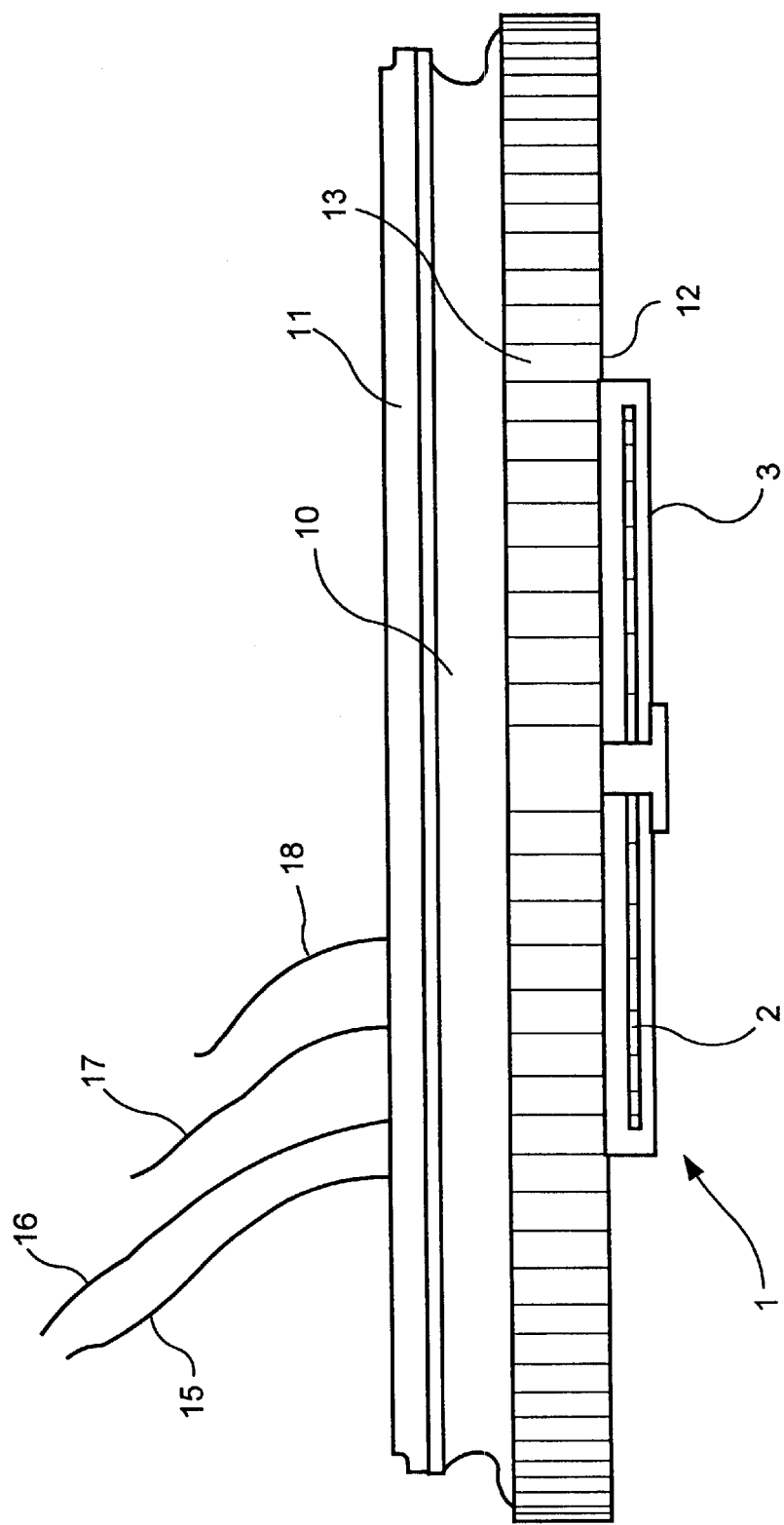
FIG. 4 is a sectional view (enlarged) of the capacitor electrode of FIGS. 1 and 1B.

As shown in FIG. 5A, the contact quality and electrical gain characteristics of the electrode-to-patient contact can be ascertained using a small injected signal on the patient ground contact. This provides a means of automatically checking the electrode hookup for problems. The idea is to apply a unit step of a few millivolts on the ground electrode of the patient. The RC network formed by the input resistor on the preamplifier 20 and the capacitive electrode 1 causes a decay in the voltage out of the preamplifier. If the contact to the patient is good, this capacity is high, in the 10 nanofarad range, and the circuit time constant is long. If the contact is poor, this capacity drops and is measured as a short time constant. This decay provides the information needed to compensate the electrode gain at low frequencies, and indicates if the capacity is less than expected because of poor contact quality. There is also a quick discharge phase that can be measured to determine the contact quality as well. The quick discharge phase can indicate the electrode has an area that is not in contact with the patient.

Figure 6:
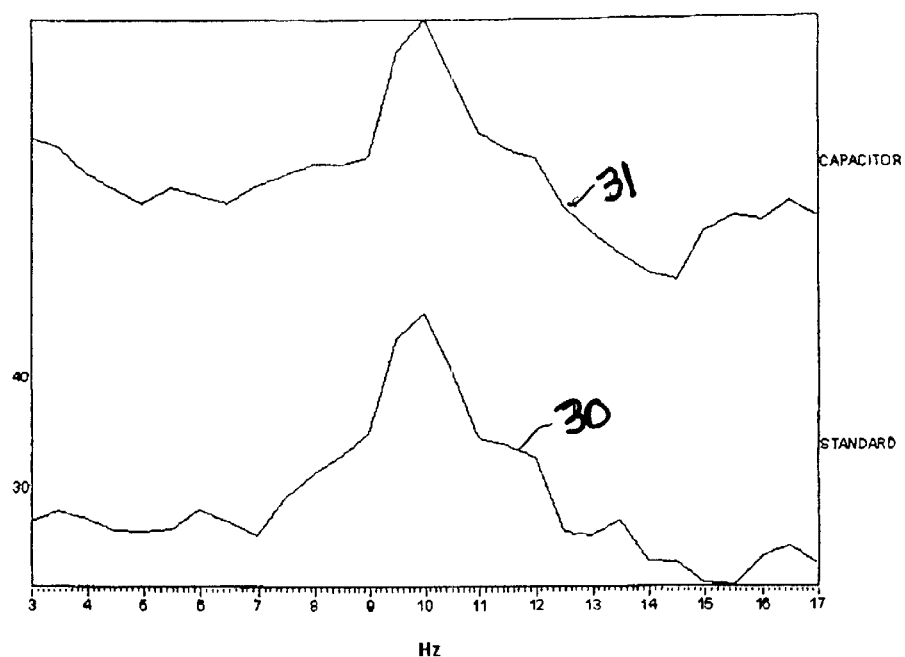
FIG. 6 is a graph showing EEG signals simultaneously recorded with the ceramic capacitor electrode of the present invention and with a conventional wet electrode for comparison.
Figure 7:
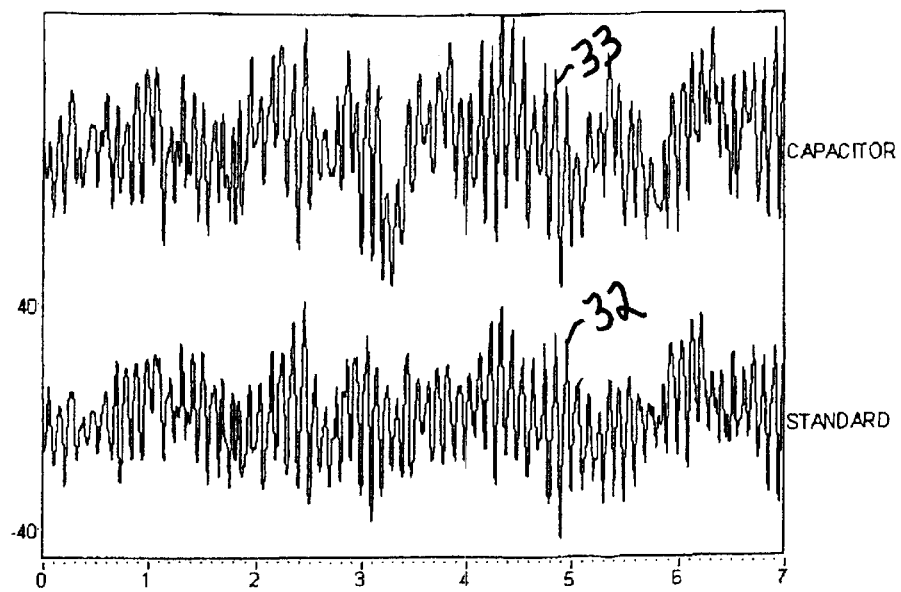
FIG. 7 is a graph showing the spectrum of EEG signals simultaneously recorded with the dry ceramic capacitor electrode of the present invention and with a conventional wet electrode for comparison.

Examples of EEG data recorded with the Ceramic Single Plate Capacitor EEG electrode are shown in FIGS. 6 and 7.

FIG. 6 shows EEG time series, with line 30 as the standard electrode and line 31 as the present capacitor electrode. FIG. 7 shows power spectra of the time series, with line 33 being the data recorded with the standard electrode and line 32 being the data recorded with the capacitor electrode. Data were recorded from a bipolar pair of electrodes located 2 cm medial to standard scalp locations F4 and P4 (10/20 EEG system). Data simultaneously recorded, with conventional wet electrodes located at F4 and P4, are also shown for comparison. The subject was recorded once in the morning and once in the afternoon in a series of conditions including resting eyes open, resting eyes closed, performing a cognitive working memory task, and generating artifacts by blinking, making patterned eye movements, clenching the jaw and moving the head. The Ceramic Single Plate Capacitor EEG Electrode performed comparably to the conventional wet electrode. However, the new electrode had a somewhat lower signal-to-noise ratio due to less than ideal electrode positioning against the scalp.

What is claimed is:

1. An electrode adapted to be removably placed on the scalp or skin of a patient to detect the patient's physiological electrical signals, the electrode comprising:
   (a) a conductive plate having an outer face and an inner face;
   (b) an insulative layer of a ceramic dielectric material which has a thickness in the range of 0.1 to 0.5 mm, the insulative layer covering the outer face of the conductive plate and adapted to contact the scalp or skin;
   (c) the insulative layer not being covered by a conductive layer so that the insulative layer is not positioned between two conductive layers as in a capacitor.

2. An electrode as in claim 1 which has a second ceramic material layer as a strengthening layer covering the inner face of the conductive plate, the second ceramic layer being in the thickness range of 0.1 to 1.0 mm.

3. An electrode as in claim 2 wherein the conductive plate is between the two insulative layers and the two insulative layers are of the same ceramic material.

4. An electrode as in claim 1 and
   a circuit board, the conductive plate being mounted on the circuit board; and
   an amplifier mounted on the circuit board and connected to the conductive plate.

5. An electrode as in claim 1 wherein the conductive plate is a metal plate.

6. An electrode as in claim 1 wherein the conductive plate is a metal disk.

7. An electrode as in claim 1 wherein the conductive plate is a metal disk having a diameter in the range of 3–10 mm.

8. An electrode as in claim 1 wherein the insulative layer is the ceramic Y5V.

9. An electrode as in claim 4 wherein the circuit board is a disk.

10. An electrode as in claim 4 wherein the circuit board is a disk having a diameter in the range of 5 mm to 13 mm.

11. An electrode which is a single plate capacitor adapted to be removably placed on the scalp of a patient to detect the patient's brain wave electrical signals, the electrode comprising:
   (a) a conductive metal plate having an outer face;
   (b) an insulative ceramic layer, having a thickness of 0.1 to 0.5 mm, covering the outer face of the plate and adapted to contact the scalp or skin;
   (c) the insulative ceramic layer not being covered by a conductive layer so that the insulative layer is not positioned between two conductive layers as in a capacitor;

(d) a circuit board, the conductive plate being mounted on the circuit board; and (e) an amplifier means mounted on the circuit board to amplify the brain wave electrical signals.

12. A method of measuring the contact quality of the electrode of claim 1 by applying a pulse or voltage step to the patient through a ground electrode, and examining the voltage which develops at the electrode.

13. An electrode adapted to be removably placed on the scalp or skin of a patient to detect the patient's physiological electrical signals, the electrode comprising:

(a) a conductive plate having an outer face and an inner face;

(b) an insulative layer of a ceramic dielectric material which has a thickness in the range of 0.002 and to 0.1 mm, the insulative layer covering the outer face of the conductive plate and adapted to contact the scalp or skin; and (c) the insulative layer not being covered by a conductive layer so that the insulative layer is not positioned between two conductive layers as in a capacitor.

14. An electrode as in claim 13 wherein the insulative layer has a thickness in the range of 0.05 and 0.1 mm.

15. An electrode as in claim 13 wherein the insulative layer is a ceramic having 0.05 mm in thickness.

* * * * *